US006495141B2

(12) United States Patent
Waggle et al.

(10) Patent No.: US 6,495,141 B2
(45) Date of Patent: *Dec. 17, 2002

(54) RECOVERY OF ISOFLAVONES FROM SOY MOLASSES

(75) Inventors: Doyle H. Waggle, St. Louis, MO (US); Barbara A. Bryan, University City, MO (US)

(73) Assignee: Protein Technologies International, Inc., St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/016,461

(22) Filed: Oct. 19, 2001

(65) Prior Publication Data

US 2002/0072591 A1 Jun. 13, 2002

Related U.S. Application Data

(60) Division of application No. 09/204,808, filed on Dec. 3, 1998, now Pat. No. 6,323,018, which is a continuation of application No. 09/086,658, filed on May 29, 1998, now Pat. No. 5,919,921, which is a continuation-in-part of application No. 08/661,845, filed on Jun. 11, 1996, now Pat. No. 5,821,361.

(51) Int. Cl.$^7$ .......................... A01N 65/00; C12N 9/24; C07D 311/36

(52) U.S. Cl. .................... 424/195.1; 424/427; 435/200; 536/8; 536/128

(58) Field of Search ............................ 435/200; 536/8, 536/128; 424/195.1, 427

(56) References Cited

U.S. PATENT DOCUMENTS

| 3,391,001 A | 7/1968 | Sair ............................. 99/17 |
| 3,461,205 A | 8/1969 | Mansfeld et al. ......... 424/195.1 |
| 3,870,805 A | 3/1975 | Hayes et al. ................ 426/148 |

(List continued on next page.)

FOREIGN PATENT DOCUMENTS

| EP | 647408 A1 | 4/1995 |
| JP | 62126185 A | 6/1987 |
| JP | 62126186 A | 6/1987 |
| JP | 63245648 A | 10/1988 |
| JP | 1-258669 | 10/1989 |
| JP | 40-36242 A | 2/1992 |
| JP | 04-266898 A | 9/1992 |
| JP | 4-283518 | 10/1992 |
| JP | 5170756 A | 7/1993 |
| JP | 6287554 A | 10/1994 |
| JP | 8214787 A | 8/1996 |
| JP | 8283283 A | 1/1997 |
| JP | 90-23822 A | 1/1997 |
| WO | WO 93/23069 | 11/1993 |
| WO | WO 97/07811 | 3/1997 |
| WO | WO 97/26269 | 7/1997 |

OTHER PUBLICATIONS

Ohta et al., *Isoflavanoid Constituents of Soybeans and Isolation of a New Acetyl Daidzin, J. Agric. Biol. Chem.*, 43(7): 1415–1419 (1979).

Ohta et al., *Isolaiton of a New Isoflavone Acetyl Glucoside, 6″–O–Acetyl Genistin from Soybeans, J. Agric. Biol. Chem.*, 44(2): 460–470 (1980).

Barbuch et al., *The Use of Thermospray Liquid Chromatography/Tandem Mass Spectrometry for the Class Identification and Structural Verification of Phytoestrogens in Soy Protein Preparations*, (1989).

Naim et al., *Antioxidative and Antihemolytic Activities of Soybean Isoflavones, J. Agric. Food Chem.*, 24(6): 1174–1177 (1976).

Grady et al., *Isoflavanoids in Root and Hypocotyl of Soybean Seedings (Glycine Max, Fabaceae), Am.J. of Bot.*, 82(8): 964–968 (1995).

Seo & Morr, *Improved High Performance Liquid Chromatographic Analysis of Phenolic Acids and Isoflavonoids from Soybean Protein Products, J. Agric. Food Chem.*, 32: 530–533 (1984).

Naim et al., *A New Isoflavone from Soya Beans, Phytochemistry*, 12: 169–170 (1973).

Kudou et al., *Malonyl Isoflavone Glycosides in Soybean Seeds, J. Agric. Biol. Chem.*, 55(9): 2227–2233 (1991).

Kudou et al., *A New Isoflavone Glycoside in Soybean Seeds (Glycine Max Merrill), Glycitein 7–O–β–D–(6″–O–Acetyl)–Glucopyranoside, J. Agric. Biol. Chem.*, 55(3): 859–860 (1991).

Huang et al. *Characterization of the Nonvolitile Minor Constituents Responsible for the Objectionable Taste of Defatted Soybean Flour, J. Food Sci.*, 47: 19–23 (1981).

Naim, *The Isolation, Characterization and Biological Activity of Isoflavones From Soybeans*, Dissertation submitted to Hebrew University of Jerusalem Oct., 1974 (Translated from Hebrew).

Matsuura and Obata, "Beta–glucosidases From Soybeans Hydrolyze Daidzin and Genistin", *J Food Science*, vol. 58; No. 1; pp. 144–147; (1993).

Naim et al., "Soybean Isoflavones Characterization, Determination and Antifungal Activity", *J. Agri. Food Chem.*, vol. 22; No. 5; pp. 806–810; (1974).

Matsuura, Obata, Fukushima, "Objectionable Flavor of Soy Milk Developed During the Soaking of Soybeans and Its Control", *J. Food Science*, vol. 54; No. 3; pp. 602–605; (1989).

(List continued on next page.)

Primary Examiner—Samuel Barts
Assistant Examiner—Devesh Khave
(74) Attorney, Agent, or Firm—Richard B. Taylor

(57) ABSTRACT

Isoflavone compositions derived from soy molasses are provided. In a first embodiment, an isoflavone material derived from soy molasses containing at least two isoflavones is provided, where at least one of the isoflavones is genistein. In a second embodiment, an isoflavone material derived from soy molasses containing at least two isoflavones is provided, where at least one of the isoflavones is daidzein.

11 Claims, No Drawings

U.S. PATENT DOCUMENTS

| | | | |
|---|---|---|---|
| 3,949,085 A | 4/1976 | Feuer et al. | 424/283 |
| 3,974,184 A | 8/1976 | Umezawa et al. | 260/345.2 |
| 4,064,277 A | 12/1977 | Yokotsuka et al. | 426/331 |
| 4,157,984 A | 6/1979 | Zilliken | 252/407 |
| 4,163,746 A | 8/1979 | Feuer et al. | 260/345.2 |
| 4,218,489 A | 8/1980 | Zilliken | 426/545 |
| 4,232,122 A | 11/1980 | Zilliken | 435/52 |
| 4,259,358 A | 3/1981 | Duthie | 426/46 |
| 4,264,082 A | 4/1981 | Zilliken | 260/345 |
| 4,366,082 A | 12/1982 | Zilliken | 252/404 |
| 4,366,248 A | 12/1982 | Zilliken | 432/125 |
| 4,390,559 A | 6/1983 | Zilliken | 426/545 |
| 4,428,876 A | 1/1984 | Iwamura | 260/123.5 |
| 4,841,077 A | 6/1989 | Ito et al. | 549/402 |
| 4,889,921 A | 12/1989 | Diosady et al. | 530/377 |
| 4,960,908 A | 10/1990 | Ito et al. | 549/403 |
| 5,141,746 A | 8/1992 | Fleury et al. | 424/195.1 |
| 5,320,949 A | 6/1994 | Shen | 435/68.1 |
| 5,352,384 A | 10/1994 | Shen | 252/398 |
| 5,424,331 A | 6/1995 | Shlyankevich | 514/456 |
| 5,506,211 A | 4/1996 | Barnes et al. | 514/27 |
| 5,516,528 A | 5/1996 | Hughes et al. | 424/464 |
| 5,554,519 A | 9/1996 | Weber et al. | 435/125 |
| 5,569,459 A | 10/1996 | Shlyankevich | 424/195.1 |
| 5,637,561 A | 6/1997 | Shen et al. | 514/2 |
| 5,637,562 A | 6/1997 | Shen et al. | 514/2 |
| 5,670,632 A | 9/1997 | Chaihorsky | 536/8 |
| 5,679,806 A | 10/1997 | Zheng et al. | 549/403 |
| 5,702,752 A | 12/1997 | Gugger et al. | 426/634 |
| 5,726,034 A | 3/1998 | Bryan et al. | 435/68.1 |
| 5,763,389 A | 6/1998 | Shen et al. | 514/2 |
| 5,789,581 A | 8/1998 | Matsuura et al. | 536/128 |
| 5,792,503 A | 8/1998 | Gugger et al. | 426/634 |
| 5,804,234 A | 9/1998 | Shu et al. | 426/69 |
| 5,821,361 A | 10/1998 | Waggle et al. | 536/128 |
| 5,827,682 A | 10/1998 | Bryan et al. | 435/68.1 |
| 5,851,792 A | 12/1998 | Shen et al. | 530/370 |
| 5,990,291 A * | 11/1999 | Waggle et al. | 536/8 |
| 5,994,508 A | 11/1999 | Bryan et al. | 530/378 |
| 6,013,771 A | 1/2000 | Shen et al. | 530/370 |
| 6,083,553 A | 7/2000 | Waggle et al. | 426/629 |
| 6,140,469 A | 10/2000 | Shen et al. | 530/370 |
| 6,323,018 B1 * | 11/2001 | Waggle et al. | 435/200 |

OTHER PUBLICATIONS

Nguyenle, T. et al., "An Investigation on the Extraction and Concentration of Isoflavones in Soy–Based Products", *J. Pharm. Biomed. Anal.*, 14:221–232: (1995).

Barnes et al., "Isoflavones and Their Conjugates in Soy Foods: Extraction Conditions and Analysis by HPLC—Mass Spectrometry", *J. Agri. Food Chem.*, vol. 42, No. 11, pp. 2466–2474 (1994).

Coward et al., "Genistein, Daidzein, and Their B–Glycoside Conjugates: Anti–tumor isoflavones in Soybean Foods From American and Asian Diets", *J. Agri. Food Chem.*, vol. 41, No. 11, pp. 1961–1967 (1993).

Walter, E. D. "Genistin (an Isoflavone Glucoside) and its Aglucone, Genistein, from Soybeans" *JACS*, vol. 63: 3273–3276, Dec. 1941.

Walz, E. "Isoflavone and Saponin Glucosides in Soya Hispida", *Annalen der Chemie*, vol. 489: 118–155, 1932.

Protein Technologies International, Inc. Internal memoranda.

Wang et al., "Isoflavone Content in Commercial Soybean Foods", J. Agric. Food Chem., vol. 42, No. 8, pp. 1666–1673 (1994).

Wang et al., "Isoflavoen Composition of American and Japanese Soybeans in Iowa: Effects of Variety, Crop Year, and Location", J. Agric. Food Chem., vol. 42, pp. 1674–1677 (1994).

Knight et al., "A Review of Phytoestrogens and Their Effects in Relation to Menopausal Symptoms", Aust. J. Nutr. Diet., vol. 53(1), pp. 5–11 (1996).

Franke et al., "Quantitation of Phytoestrogens in Legumes by HPLC", J. Agric. Food Chem., vol. 42, pp. 1905–1913 (1994).

Cook et al., "Flavonoids—Chemistry, Metabolism, Cardioprotective Effects, and Dietary Sources", J. Nutr. Biochem., vol. 7, pp. 66–76 (1996).

Murphy, "Phytoestrogen Content of Processed Soybean Products", Food Technology, pp. 60, 62–64 (Jan. 1982).

Eldridge, "Determination of Isoflavones in Soybean Flours, Protein Concentrates, and Isolates", J. Agric. Food Chem., vol. 30, pp. 353–355 (1982).

* cited by examiner

RECOVERY OF ISOFLAVONES FROM SOY MOLASSES

This application is a divisional application of patent application Ser. No. 09/204,808, filed on Dec. 3, 1998 is now U.S. Pat. No. 6,323,018, which is a continuation application of patent application Ser. No. 09/086,658 filed on May 29, 1998 now U.S. Pat. No. 5,919,921, which is a continuation-in-part application of patent application Ser. No. 08/661,845 filed on Jun. 11, 1996, now U.S. Pat. No. 5,821,361.

FIELD OF THE INVENTION

The present invention relates to processes for recovering isoflavones from soy molasses. In addition, the present invention relates to the resulting products containing isoflavones.

BACKGROUND OF THE INVENTION

Isoflavones occur in a variety of leguminous plants, including vegetable protein materials such as soybeans. These compounds include daidzin, 6"-OAc daidzin, 6"-OMal daidzin, daidzein, genistin, 6"-OAc genistin, 6"-OMal genistin, genistein, glycitin, 6"-OAc-glycitin, 6"-OMal glycitin, glycitein, biochanin A, formononentin, and coumestrol. Typically these compounds are associated with the inherent, bitter flavor of soybeans.

The isoflavones in soybean materials include isoflavone glucosides (glucones), isoflavone conjugates and aglucone isoflavones. Isoflavone glucosides have a glucose molecule attached to an isoflavone moiety. Isoflavone conjugates have additional moieties attached to the glucose molecule of an isoflavone glucoside, for example, 6"-OAc genistin contains an acetate group attached to the six position of the glucose molecule of genistin. Aglucone isoflavones consist solely of an isoflavone moiety.

Soy contains three "families" of isoflavone compounds having corresponding glucoside, conjugate, and aglucone members: the genistein family, the daidzein family, and the glycitein family. The genistein family includes the glucoside genistin; the conjugates 6"-OMal genistin (6"-malonate ester of genistin) and 6"-OAc genistin (6"-acetate ester of genistin); and the aglucone genistein. The daidzein family includes the glucoside daidzin; the conjugates 6"-OMal daidzin and 6"-OAc daidzin; and the aglucone daidzein. The glycitein family includes the glucoside glycitin; the conjugate 6"-OMal glycitin; and the aglucone glycitein.

In the production of commercial products, such as vegetable protein concentrates, the focus has been to remove these materials. For example, in a conventional process for the production of a soy protein concentrate in which soy flakes are extracted with an aqueous acid or an aqueous alcohol to remove water soluble materials from the soy flakes, much of the isoflavones are solubilized in the extract. The extract of water soluble materials, including the isoflavones, is soy molasses. The soy molasses is a byproduct material in the production of soy protein concentrate which is typically discarded. Soy molasses, therefore, is an inexpensive and desirable source of isoflavones, provided that the isoflavones can be separated from the soy molasses.

It has recently been recognized that the isoflavones contained in vegetable protein materials such as soybeans have medicinal value. The aglucone isoflavones are of particular interest. Genistein and daidzein may significantly reduce cardiovascular risk factors. "Plant and Mammalian Estrogen Effects on Plasma Lipids of Female Monkeys", *Circulation*, vol. 90, p. 1259 (October 1994). Genistein and daidzein are also thought to reduce the symptoms of conditions caused by reduced or altered levels of endogenous estrogen in women, such as menopause or premenstrual syndrome. Further, it has recently been recognized that aglucone isoflavones may inhibit the growth of human cancer cells, such as breast cancer cells and prostate cancer cells, as described in the following articles: "Genistein Inhibition of the Growth of Human Breast Cancer Cells, Independence from Estrogen Receptors and the Multi-Drug Resistance Gene" by Peterson and Barnes, *Biochemical and Biophysical Research, Communications*, Vol. 179, No. 1, pp. 661–667, Aug. 30, 1991; "Genistein and Biochanin A Inhibit the Growth of Human Prostrate Cancer Cells but not Epidermal Growth Factor Receptor Tyrosine Autophosphorylation" by Peterson and Barnes, *The Prostate*, Vol. 22, pp. 335–345 (1993); and "Soybeans Inhibit Mammary Tumors in Models of Breast Cancer" by Barnes, et al., *Mutagens and Carcinogens in the Diet*, pp. 239–253 (1990).

The aglucone isoflavones have the following general formula:

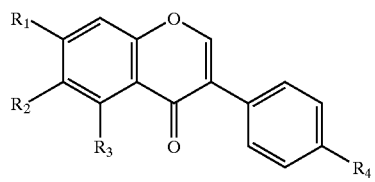

wherein, $R_1$, $R_2$, $R_3$ and $R_4$ may be selected from the group consisting of H, OH and $OCH_3$. Genistein has the formula above where $R_1$=OH, $R_2$=H, $R_3$=OH, and $R_4$=OH, daidzein has the formula above where $R_1$=OH, $R_2$=H, $R_3$=H, and $R_4$=OH, and glycitein has the formula above where $R_1$=OH, $R_2$=$OCH_3$, $R_3$=H, and $R_4$=OH.

It is therefore to the isoflavones and to the recovery of an isoflavone enriched material from soy molasses to which the present invention is directed. The present invention is further directed to isoflavone glucosides and aglucone isoflavones—to the conversion of isoflavones of soy molasses to isoflavone glucosides and aglucone isoflavones, and to the recovery of an isoflavone glucoside enriched material and an aglucone isoflavone enriched material from soy molasses.

A general process for converting vegetable protein isoflavone conjugates to aglucone isoflavones is known, and is provided in the currently pending application U.S. Ser. No. 08/477,102 filed Jun. 7, 1995 owned by the assignee of the present application.

Other processes are known in the art for converting isoflavone glucosides to aglucone isoflavones, such as described in Japanese Patent Application 258,669 to Obata, et al. Such processes do not provide for the recovery of an isoflavone enriched material from soy molasses. Such processes also do not provide for the conversion of isoflavone conjugates to isoflavone glucosides or to aglucone isoflavones. Furthermore, these processes achieve only a moderate extent of conversion of isoflavone glucosides to aglucone isoflavones, and require a substantial period of time to effect this moderate extent conversion.

It is therefore an object of the present invention to provide an isoflavone enriched material and a process for producing the same from soy molasses.

It is a further object of the present invention to provide an isoflavone glucoside enriched material and a process for producing the same from soy molasses.

It is still a further object of the present invention to provide an aglucone isoflavone enriched material and a process for producing the same from soy molasses.

SUMMARY OF THE INVENTION

The present invention is an isoflavone enriched material and a process for recovering the same from a soy molasses material containing isoflavones. The method comprises providing a soy molasses material containing isoflavones, and separating a cake from the soy molasses material at a pH and a temperature sufficient to cause a majority of the isoflavones to be contained in the cake. Preferably the pH is about 3.0 to about 6.5 and the temperature is about 0° C. about 35° C. during the separation. The cake is an isoflavone enriched material.

In one embodiment, a glucoside enriched isoflavone material is formed from the cake of isoflavone enriched material. An aqueous slurry is formed of the isoflavone enriched material. The slurry is treated at a temperature of about 2° C. to about 120° C. and a pH of about 6 to about 13.5 for a time sufficient to convert isoflavone conjugates in the isoflavone enriched material to isoflavone glucosides. A cake of isoflavone glucoside enriched material may then be separated from the slurry.

In another embodiment, an aglucone isoflavone enriched material is formed from the cake of isoflavone enriched material. An aqueous slurry is formed of the isoflavone enriched material. The slurry is treated at a temperature of about 2° C. to about 120° C. and a pH of about 6 to about 13.5 for a time sufficient to convert isoflavone conjugates in the isoflavone enriched material to isoflavone glucosides. An enzyme capable of cleaving 1,4-glucoside bonds is contacted with the isoflavone glucosides in the slurry at a temperature of about 5° C. to about 75° C. and a pH of about 3 to about 9 for a time sufficient to convert the isoflavone glucosides to aglucone isoflavones. A cake of aglucone isoflavone enriched material may be separated from the slurry.

In another aspect, the present invention is an isoflavone glucoside enriched material and a process for recovering the same from soy molasses. The soy molasses is treated at a temperature of from about 2° C. to about 120° C. and at a pH value of between about 6 to about 13.5 for a time period sufficient to convert isoflavone conjugates contained in the soy molasses to isoflavone glucosides. A cake of isoflavone glucoside enriched material is separated from the soy molasses material at a pH and a temperature sufficient to cause a majority of the isoflavone glucosides to be contained in the cake.

In another aspect, the present invention is an aglucone isoflavone enriched material, and a process for recovering the same from soy molasses. The soy molasses is treated at a temperature of from about 2° C. to about 120° C. and at a pH value of between about 6 to about 13.5 for a time period sufficient to convert isoflavone conjugates contained in the soy molasses to isoflavone glucosides. An enzyme capable of cleaving 1,4-glucoside bonds is contacted with the isoflavone glucosides in the soy molasses material at a temperature of about 5° C. to about 75° C. and a pH of about 3 to about 9 for a time period sufficient to convert the isoflavone glucosides to aglucone isoflavones. A cake of aglucone isoflavone enriched material is separated from the soy molasses material at a pH and a temperature sufficient to cause a majority of the aglucone isoflavones to be contained in the cake.

DETAILED DESCRIPTION OF PREFERRED EMBODIMENTS

The starting material of a process of the present invention may be soy molasses. Soy molasses is generally considered to be the soy solubles removed from soy insolubles by washing with alcohol or aqueous acid. Soy solubles included in the soy molasses are primarily carbohydrates, highly soluble protein, and isoflavones. Soy insolubles not included in the soy molasses include vegetable fiber materials, insoluble soy protein, cellulose, and insoluble hemicellulose. Soy molasses is a by-product of many commercial processes involving soybeans or soybean derivatives, such as processes for producing protein concentrate products. Accordingly, soy molasses is produced in large quantities to such an extent that soy molasses is a relatively inexpensive commercially available commodity.

Alternatively, the starting material for a process of the present invention may be a soy material which contains isoflavones and carbohydrates from which a soy molasses may be formed. Such soy materials include, but are not limited to, soy meal, soy flour, soy grits, soy flakes, and mixtures thereof, which preferably have been chemically or mechanically defatted.

The starting soy material is extracted or washed with an extractant effective to remove substantial amounts of the isoflavones and carbohydrates present in the soy material. After the extraction or wash, the resulting extract is separated from the insoluble residual soy materials to form a soy molasses. The extractant preferably is selected from an aqueous low molecular weight alcohol solution, or an aqueous solution having a pH at about the isoelectric point of soy protein. For example, preferred aqueous alcohols include aqueous methanol, aqueous ethanol, aqueous isopropyl alcohol, and aqueous propanol, where the alcohol to water ratio of the solution is preferably at least 40:60, and more preferably is at least 60:40, and most preferably falls within a range of from 65:35 to 90:10. A preferred aqueous solution having a pH at about the isoelectric point of soy protein is water adjusted with a suitable acid, preferably a mineral acid such as hydrocholoric acid or sulfuric acid, to a pH of from about 3.5 to about 5.5, more preferably to a pH of from about 4 to about 5, and most preferably to a pH of from about 4.4 to about 4.6.

In a preferred embodiment, the soy molasses is produced from defatted soy flakes from which oil has been removed by solvent extraction in a conventional manner. The defatted soy flakes are extracted with water which has been adjusted to an acidic pH, preferably about pH 4 to about pH 5, by the addition of one or more suitable acids such as acetic acid, sulfuric acid, phosphoric acid, hydrochloric acid or any other suitable reagent. Preferably the ratio of the acidic extractant to soy flakes is about 10:1 to about 20:1 by weight, and more preferably from about 12:1 to about 16:1. To improve the efficacy of the extraction, the temperature of the extractant may be elevated above room temperature, preferably between about 32° C. and about 55° C. After the extraction, the soy molasses is removed from the soy insolubles.

In another embodiment, defatted soy flakes are extracted with aqueous alcohol to produce the soy molasses. Preferably, the flakes are extracted with about 80% aqueous ethanol at a ratio of about 10:1 to about 20:1 by weight of extractant to soy flakes, and more preferably from about 12:1 to about 16:1 by weight of extractant to soy flakes. The temperature of the alcohol extractant may be elevated above room temperature, preferably from about 32° C. to about 55° C., to improve the efficacy of the extraction. The soy molasses is then removed from the soy insolubles The soy molasses is then condensed. The soy molasses may be condensed by conventional methods for removing a liquid, including, but not limited to, evaporation, preferably under reduced pressure, steam stripping, or distillation. The condensed soy molasses may contain at least 10% solids, by weight, and preferably contains from about 25% to about 60% solids, by weight, and more preferably contains from about 30% to about 50% solids, by weight. For example, condensed soy molasses is typically an aqueous mixture containing about 50% or more solids that comprise about 6% (based on the total weight of the soy molasses) protein, about 3% ash, about 5% fat, and about 36% carbohydrates. "Soy molasses material" as that term is used herein refers to a composition containing soy molasses, a condensed soy molasses, and/or derivatives of soy molasses such as an isoflavone glucoside enriched soy molasses material and an aglucone isoflavone enriched soy molasses material. Accordingly, these terms are used interchangeably herein.

An isoflavone enriched material may be recovered from the condensed soy molasses material. The condensed soy molasses material may be diluted with water to a solids content of from about 6% to about 13%, with 13% being most preferred. Dilution of the condensed soy molasses material is not a requirement for the process, however, diluting the relatively thick condensed soy molasses material facilitates processing the material.

The condensed soy molasses material, preferably diluted, is treated at a pH and a temperature at which a majority of the isoflavones will separate from the liquid fraction of the condensed soy molasses upon performing a separation procedure. In a preferred embodiment, the condensed soy molasses material is treated at a pH of about 3.0 to about 6.5 and a temperature of about 0° C. to about 35° C. to maximize the insolubility of the isoflavones in the liquid fraction of the condensed soy molasses. Isoflavones may be separated from the liquid fraction of the condensed soy molasses at pH values outside the preferred range and at temperatures above 35° C., however, these conditions are less preferred since less isoflavones are separated in the separation procedure. The pH of the condensed soy molasses may be adjusted with a suitable conventional acidic or basic reagent, if necessary. It is most preferred that the pH of the condensed soy molasses be adjusted to about 4.5. It is also preferred to chill or cool the condensed soy molasses to a temperature of about 0° C. to about 10° C., and most preferably to a temperature of about 4° C. to about 7° C.

The condensed soy molasses material is then subjected to a separation procedure to separate a cake of isoflavone enriched material from the liquid fraction of the condensed soy molasses material. The separation is performed while the soy molasses material is maintained under the previously described pH and temperature conditions.

In one embodiment, the cake of isoflavone enriched material is separated by centrifuging the soy molasses material and decanting the supernatant from the cake. Centrifugation is preferably performed at about 3,000 to about 10,000 rpm for approximately 30 minutes at about 0° C. to about 10° C.

In another embodiment, the isoflavone enriched cake may be separated from the soy molasses material by filtration. Preferably the filtration is done at the previously described pH and temperature conditions, most preferably at a pH of about 4.5 and a temperature of about 0° C. to about 10° C.

The separated cake of isoflavone enriched material contains a significant amount of isoflavones therein. Preferably the cake of isoflavone enriched material contains at least 20 mg of isoflavones per gram of cake material, on a dry basis (at least about 2% isoflavones by weight) and more preferably contains from about 20 mg to about 50 mg of isoflavones per gram of cake material (from about 2% to about 5% isoflavones, by weight).

In another aspect of the present invention, a cake of isoflavone glucoside enriched material may be recovered from soy molasses. A soy molasses material is obtained as described above. Although not a requirement, it is preferred that the soy molasses material be a condensed soy molasses material diluted to a solids content of from about 6% to about 13%, and most preferably about 13%, to facilitate processing the material.

A conversion operation is then performed on the soy molasses material to convert isoflavone conjugates in the soy molasses material to isoflavone glucosides. A substantial portion of the isoflavones in the soy molasses material are isoflavone conjugates, therefore the conversion substantially increases the amount of isoflavone glucosides in the soy molasses material. The conversion has been found to be dependent on the pH and the temperature of the soy molasses material.

The pH range for conversion of the isoflavone conjugates to isoflavone glucosides in a soy molasses material is from about 6 to about 13.5. The pH of the soy molasses should be adjusted to the desired pH, if necessary, with a suitable base, caustic agent, or basic reagent if the pH is to be raised, or, if the pH is to be lowered, with a suitable acid or acid reagent. The conversion of isoflavone conjugates to isoflavone glucosides has been found to be base catalyzed, and so it is most preferred to utilize a high pH to achieve rapid conversion. The most preferred pH for conversion of the isoflavone conjugates to isoflavone glucosides is a pH of about 9 to about 11.

The temperature range for conversion of the isoflavone conjugates to isoflavone glucosides in soy molasses is from about 2° C. to about 120° C. The temperature range at which the conversion readily occurs depends on the pH of the soy molasses material. The inventors have found that the conversion occurs easily at lower temperatures when the pH is relatively high. For example, at a pH of about 11 the conversion occurs rapidly and efficiently at a temperature range of about 5° C. to about 50° C. At a pH of about 9 conversion occurs efficiently within a temperature range of about 45° C. to about 75° C. When the pH of the soy molasses material is relatively low, the conversion occurs at higher temperatures. For example, at a pH of about 6, the conversion occurs within a temperature range of about 80° C. to about 120° C. In a preferred embodiment, the conversion is effected at about 35° C. and a pH of about 11. In another preferred embodiment, the conversion is effected at a temperature of about 73° C. and a pH of about 9.

The time period required for conversion of isoflavone conjugates to isoflavone glucosides depends primarily upon the pH and temperature range utilized in the soy molasses material. Such conversion times typically range from about 15 minutes up to several hours or longer. Conversion occurs more rapidly at a higher pH and at a higher temperature. At a pH of about 9, conversion is substantially complete in about 4 hours to about 6 hours at 73° C. In a most preferred embodiment, the isoflavone conjugates are converted to isoflavone glucosides in about 30 minutes to about 1 hour, preferably about 45 minutes, at a pH of about 11 and at a temperature of about 35° C.

The conversion of the isoflavone conjugates to isoflavone glucosides is remarkably efficient, converting at least a majority, and preferably substantially all of the isoflavone conjugates present to isoflavone glucosides. The term a "majority" refers to an extent of conversion of at least about 50%. The term "substantially all" refers to an extent of conversion of at least about 80%, and most preferably at least about 90%.

Following the conversion of the isoflavone conjugates to isoflavone glucosides, a cake of isoflavone glucoside enriched material may be separated from the soy molasses material. The soy molasses is condensed by conventional means, if the soy molasses material is not already condensed. The condensed soy molasses material is treated at a pH and a temperature at which a majority of the isoflavone glucosides will separate from the liquid fraction of the condensed soy molasses material in a separation procedure. In a preferred embodiment the condensed soy molasses material is maintained at a pH of about 3 to about 6.5, most preferably about 4.5, and at a temperature of about 0° C. to about 35° C., preferably about 0° C. to about 10° C., and most preferably about 4° C. to about 7° C., during the separation process. The pH of the condensed soy molasses material may be adjusted with a suitable conventional acidic or basic reagent, if necessary.

The separation may be effected by conventional means for separating solids from a liquid. The isoflavone glucoside enriched cake is preferably separated by centrifugation or filtration as described above with respect to separating an isoflavone enriched cake from the liquid fraction of a condensed soy molasses material.

The separated cake of isoflavone glucoside enriched material contains a significant amount of isoflavone glucosides therein. Preferably the cake of isoflavone glucoside enriched material contains at least 20 mg of isoflavone glucosides per gram of cake material, on a dry basis (at least about 2% isoflavone glucosides by weight) and more preferably contains from about 20 mg to about 50 mg of isoflavone glucosides per gram of cake material (from about 2% to about 5% isoflavone glucosides, by weight).

In yet another aspect of the invention, a cake of aglucone isoflavone enriched material may be recovered from soy molasses. A soy molasses material is obtained as described above, preferably a condensed soy molasses material diluted with water to a solids content of about 6% to about 13%. The soy molasses material is treated to convert the isoflavone conjugates to isoflavone glucosides as described above.

An enzymatic conversion operation is then performed on the isoflavone glucoside enriched soy molasses material by contacting a suitable enzyme with isoflavone glucosides in the soy molasses material at a suitable pH and temperature to convert the isoflavone glucosides to aglucone isoflavones. The two-step conversion process effectively converts substantially all of the isoflavone conjugates and isoflavone glucosides in the soy molasses material to aglucone isoflavones, substantially increasing the amount of aglucone isoflavones in the soy molasses material.

The conversion of isoflavone glucosides to aglucone isoflavones has been found to be dependent on a variety of factors including the type of enzymes present in the soy molasses material, distribution of enzyme concentrations, activities of the enzymes, and the pH and temperature of the soy molasses material during the conversion. The enzymes required to effect the conversion are enzymes capable of cleaving the glucosidic linkage between the isoflavone moiety and the glucose molecule of the isoflavone glucosides. In a preferred embodiment, the enzymes are saccharidase or gluco-amylase enzymes capable of cleaving 1,4-glucoside bonds. The enzymes may be inherently present in the soy molasses material, or may be commercially available enzymes which are added to the soy molasses material. Inherently present enzymes are referred to herein as "residual" enzymes, and enzymes that are added to the soy molasses material are referred to herein as "supplemental" enzymes.

Sufficient enzyme should be present in the soy molasses material to convert at least a majority, and preferably substantially all, of the isoflavone glucosides to aglucone isoflavones. Generally, if the residual enzymes in the soy molasses material are insufficient to effect the conversion, supplemental enzymes should be added to the soy molasses material. In a preferred embodiment, supplemental enzymes are added to the soy molasses material regardless of whether sufficient residual enzymes are present in the soy molasses material since addition of supplemental enzymes dramatically decreases the time necessary to effect substantially complete conversion of the glucosides to aglucones. If supplemental enzymes are added, the supplemental enzymes should be added so that the total concentration of enzyme present is about 0.1% to about 10% by weight of the solids in the soy molasses material on a dry basis.

Supplemental enzymes are selected based on optimum activity at selected pH and temperature conditions, and cost effectiveness. The supplemental enzymes are enzymes capable of cleaving the bond between the isoflavone moiety and the glucose molecule of the isoflavone glucosides, such as saccharidase and gluco-amylase enzymes capable of cleaving 1,4-glucoside bonds. Preferred supplemental enzymes are commercially available alpha-and beta-glucosidase enzymes, beta-galactosidase enzymes, gluco-amylase enzymes, and pectinase enzymes. Particularly preferred are enzymes such as Biopectinase 100L (which is preferably utilized at a pH range of from about 3 to about 6), Biopectinase 300L (optimum pH range from about 3 to about 6), Biopectinase OK 70L (optimum pH range from about 3 to about 6), Biolactase 30,000 (optimum pH range from about 3 to about 6) Neutral Lactase (optimum pH range from about 6 to about 8), all of which are available from Quest International, 1833 57th Street, Post Office Box 3917, Sarasota, Fla. 34243. Also especially preferred are Lactase F (which is preferably utilized at a pH range of from about 4 to about 6), and Lactase 50,000 (optimum pH range from about 4 to about 6), both available from Amano International Enzyme Co., Inc., Post Office Box 1000, Troy, Va. 22974. Other particularly preferred supplemental enzymes include G-Zyme G990 (optimum pH from about 4 to about 6) and Enzeco Fungal Lactase Concentrate (optimum pH from about 4 to about 6) available from Enzyme Development Corporation, 2 Penn Plaza, Suite 2439, New York, N.Y. 10121; Lactozyme 3000L (which preferably is utilized at a pH range from about 6 to about 8), and Alpha-Gal 600L (which preferably is utilized at a pH range of from about 4 to about 6.5), available from Novo Nordisk Bioindustrials, Inc., 33 Turner Road, Danbury, Conn. 06813; Maxilact L2000 (which is preferably utilized at a pH range of from about 4 to about 6), available from Gist Brocades Food Ingredients, Inc., King of Prussia, Pa., 19406; and Neutral Lactase (which is preferably utilized at a pH range of from about 6 to about 8), available from Pfizer Food Science Group, 205 East 42nd Street, New York, N.Y. 10017.

The pH range for conversion of the isoflavone glucosides to aglucone isoflavones is from about 3 to about 9. The pH that is utilized depends primarily upon the type of enzyme used, and should be selected accordingly. The residual enzyme is active within a pH range of about 7 to about 9, although it is believed that the pH of the soy molasses material is lowered during the course of the conversion. The supplemental enzymes are active within an optimum pH range specified by the manufacturer of the enzyme, as shown above for several specific enzymes. Typically the supplemental enzymes are active either in a neutral pH range from about 6 to about 8, or in an acidic pH range from about 3 to about 6.

The pH of the soy molasses material may be adjusted to a desired value for conducting the conversion of isoflavone glucosides to aglucone isoflavones. In most instances the pH is reduced from the relatively high or basic pH required to convert the isoflavone conjugates to isoflavone glucosides by the addition of one or more suitable acids such as acetic acid, sulfuric acid, phosphoric acid, hydrochloric acid, or any other suitable reagent.

The temperature range of the soy molasses material for the conversion of glucosides to aglucones is from about 5° C. to about 75° C. The temperature significantly affects the activity of the enzymes, and therefore, the rate of conversion. The supplemental enzymes may be active above 70° C., for example Alpha-Gal 600L is active at 75° C., however, it is preferred to conduct the conversion at lower temperatures to avoid enzyme deactivation. In a preferred embodiment, the conversion is effected between about 35° C. and about 45° C.

The time required for conversion of the glucosides to aglucones depends upon enzyme-related factors, particularly concentration, and the temperature and pH of the system. In most instances it is possible to achieve substantially complete conversion within 24 hours, however, it is preferred that supplemental enzyme be added to dramatically increase the rate of the reaction. The selected supplemental enzyme, enzyme concentration, pH and temperature preferably cause substantially complete conversion within about 2 hours, and most preferably within about 1 hour.

The conversion of the isoflavone glucosides to aglucone isoflavones is remarkably efficient, converting at least a majority, and preferably substantially all of the glucosides present to aglucones. The term "a majority" refers to an extent of conversion of at least about 50%. The term "substantially all" refers to an extent of conversion of at least about 80%, and most preferably at least about 90%.

Following the conversion of the isoflavone glucosides to aglucone isoflavones the soy molasses material is condensed as described above, if the soy molasses material has not already been condensed. A cake of aglucone isoflavone enriched material may be separated from the liquid fraction of the condensed soy molasses material. The soy molasses material is treated at a pH and a temperature at which a majority of the aglucone isoflavones will separate from the liquid fraction of the condensed soy molasses material in a separation procedure. Preferably, the condensed soy molasses material is maintained at a pH of about 3 to about 6.5, most preferably about 4.5, and at a temperature of about 0° C. to about 35° C., preferably about 0° C. to about 10° C., and most preferably about 4° C. to about 7° C., during the separation process. The pH of the condensed soy molasses material may be adjusted with a suitable conventional acidic or basic reagent, if necessary.

The separation may be effected by conventional means for separating solids from a liquid. The aglucone isoflavone enriched cake is preferably separated by centrifugation or filtration as described above with respect to separating an isoflavone enriched cake from the liquid fraction of a condensed soy molasses material.

The separated cake of aglucone isoflavone enriched material contains a significant amount of aglucone isoflavones therein. Preferably the cake of aglucone isoflavone enriched material contains at least 20 mg of aglucone isoflavones per gram of cake material, on a dry basis (at least about 2% aglucone isoflavones by weight) and more preferably contains from about 20 mg to about 50 mg of aglucone isoflavones per gram of cake material (from about 2% to about 5% aglucone isoflavones, by weight).

An aglucone isoflavone enriched material may also be produced from an isoflavone enriched material recovered from soy molasses, where the process for recovering an isoflavone enriched material from soy molasses is described above. Water is added to the recovered cake of isoflavone enriched material to form a slurry of the isoflavone enriched material. Preferably the slurry is diluted to about 6% to about 13% solids, although a higher solids content may be used. Isoflavone conjugates in the slurry are then converted to isoflavone glucosides by treating the slurry under the same conditions described above with respect to converting isoflavone conjugates to isoflavone glucosides in soy molasses. In particular, the slurry is treated at a pH of about 6 to about 13.5, preferably about pH 9 to about pH 11, and a temperature of about 2° C. to about 120° C. for a period of about 15 minutes to several hours. Most preferably the slurry is treated at a pH of about 11 and a temperature of about 5° C. to about 50° C., preferably about 35° C., for a period of about 30 minutes to about 1 hour; or at a pH of about 9 and a temperature of about 45° C. to about 75° C., preferably about 73° C., for a period of about 4 hours to about 6 hours. If desired, an isoflavone glucoside enriched material may be separated from the slurry in a manner similar to the separation of an isoflavone enriched material from soy molasses described above.

Isoflavone glucosides in the slurry are then converted to aglucone isoflavones under the same conditions described above with respect to converting isoflavone glucosides to aglucone isoflavones in a soy molasses material. In particular, the isoflavone glucosides in the slurry are contacted with an enzyme capable of cleaving the glucosidic linkage between the isoflavone moiety and the glucose molecule of the isoflavone glucosides under suitable pH and temperature conditions for a period of time sufficient to convert the isoflavone glucosides to aglucone isoflavones. Preferred enzymes, pH conditions, temperatures, and time periods are described above. An aglucone isoflavone enriched material may be separated from the slurry in a manner similar to the separation of an isoflavone enriched material from soy molasses described above.

An aglucone isoflavone enriched material may also be produced from an isoflavone glucoside enriched material recovered from a soy molasses material, where the process for recovering an isoflavone glucoside enriched material from a soy molasses material is described above. Water is added to the recovered cake of isoflavone glucoside enriched material to form a slurry of the isoflavone glucoside enriched material. Preferably the slurry is diluted to about 6% to about 13% solids, although a higher solids content may be used. The isoflavone glucosides in the slurry are converted to aglucone isoflavones in the same manner described above with respect to the isoflavone glucoside enriched slurry formed from an isoflavone enriched slurry. An aglucone isoflavone enriched material may be separated from the slurry after the conversion in a manner similar to the separation of an isoflavone enriched material from soy molasses described above.

EXPERIMENTAL

The present invention is illustrated in more detail by the following examples. The examples are intended to be illustrative, and should not be interpreted as limiting or otherwise restricting the scope of the invention in any way.

As noted above, soy materials, including soy molasses, include the genistein, daidzein, and glycitein "families" of isoflavones having corresponding glucoside, conjugate, and aglucone members, where the genistein family contains the conjugates 6"-OMal genistin, 6"-OAc genistin, the glucoside genistin, and the aglucone genistein; the daidzein family contains the conjugates 6"-OMal daidzin, 6"-OAc daidzin, the glucoside daidzin, and the aglucone daidzein; and the glycitein family includes the conjugate 6"-OMal glycitin, the glucoside glycitin, and the aglucone glycitein. In the following examples the relative concentrations of isoflavones are measured either as a total concentration of an isoflavone family, or as individual percentages of each isoflavone in a family of isoflavones. For example, the total concentration of the genistein family of isoflavones is the sum of the concentrations of 6"-OMal genistin, 6"-OAc genistin, genistin, and genistein, and the percentage of each of the isoflavones in the genistein family is determined relative to the other genistein family isoflavones: % genistin+% 6"OMal genistin+% 6"OAc genistin+% genistein=100%.

EXAMPLE 1

In a first experiment, the recovery of an isoflavone enriched material from soy molasses is examined at various concentrations of soy molasses. The total concentration of each isoflavone family is measured in a soy molasses sample having a selected concentration, in a cake separated from the soy molasses sample according to the method of the invention, and in the liquid whey from which the cake is removed by the separation procedure.

Soy molasses is analyzed for the total concentration of all forms of isoflavones present. Samples of the soy molasses are diluted with water to a solids content of 28% (1:2 dilution), 13.7% (1:4 dilution), and 6.6% (1:8 dilution). All samples are pH adjusted to 4.5. The treated samples are then centrifuged at a rate of between 3000 rpm for 30 minutes to separate and produce liquid whey and cake portions from the samples. One set of samples is centrifuged at a temperature of 0.6° C. Samples having 28% and 13.7% soy molasses solids are centrifuged at a temperature of 60° C. for comparison with samples having the same concentration of soy molasses solids that are separated at 0.6° C. The resulting liquid and cake portions of the samples are analyzed for the total concentration of all forms of isoflavones present.

Table 1 sets forth the concentrations of isoflavones in the various cake and liquid fractions obtained from the previously described testing. The indicated totals are the totals of all forms of the particular isoflavone including conjugates, glucoside, and aglucone forms expressed in mg of isoflavone per gram of cake or liquid fraction solids.

TABLE 1

| Sample | Total Genistein (family) mg/g | Total Daidzein (family) mg/g | Total Glycitein (family) mg/g |
|---|---|---|---|
| Soy Molasses Starting Material Not separated | 6.1 | 4.8 | 1.0 |
| 1:2 Dilution (28% solids) Whey separated at 0.6° C. | 28 | 3.0 | 0.6 |
| 1:2 Dilution | 16.9 | 10.9 | 1.9 |

TABLE 1-continued

| Sample | Total Genistein (family) mg/g | Total Daidzein (family) mg/g | Total Glycitein (family) mg/g |
|---|---|---|---|
| Cake separated at 0.6° C. 1:2 Dilution | 3.8 | 4.0 | 0.8 |
| Whey separated at 60° C. 1:2 Dilution | 14.1 | 8.2 | 1 5 |
| Cake separated at 60° C. 1:4 Dilution (13.7% solids) | 3.0 | 3.4 | 0.7 |
| Whey separated at 0.6° C. 1:4 Dilution | 18.3 | 11.0 | 2.0 |
| Cake separated at 0.6° C. 1:4 Dilution | 4.4 | 4.3 | 0.8 |
| Whey separated at 60° C. 1:4 Dilution | 13.4 | 7.2 | 1.5 |
| Cake separated at 60° C. 1:8 Dilution (6.6% solids) | 4.3 | 4.5 | 0.9 |
| Whey separated at 0.6° C. 1:8 Dilution | 20.1 | 10.2 | 2.1 |
| Cake separated at 0.6° C. | | | |

In all separated samples, the concentration of isoflavones is significantly higher in the cake than in soy molasses starting material and much higher than the concentration of isoflavones in the liquid whey fraction solids. The samples separated at 0.6° C. contained a higher concentration of isoflavones in the cake than corresponding samples separated at 60° C., which had higher concentrations of isoflavones in the whey fraction solids.

EXAMPLE 2

In another experiment, the recovery of an isoflavone glucoside enriched material from soy molasses is examined. Isoflavone conjugates in the soy molasses are converted to isoflavone glucosides, and an isoflavone glucoside enriched cake is separated from the soy molasses material. The extent of conversion is determined by the quantitative decrease of the percentage and concentration of malonate and acetate esters of an isoflavone family coupled with a corresponding quantitative increase of the percentage of the glucoside of the same isoflavone family.

Soy molasses starting material is analyzed for concentration of individual isoflavone compounds. Two samples of the soy molasses material are made by diluting the soy molasses with water in the following ratios: 1:4(100 g of molasses+300 g water); and 1:8(50 g of molasses+350 g water). The pH of the samples is adjusted to 11, and the temperature of the samples is held at 35° C. for 30 minutes. The pH of the samples is then adjusted to 4.5 and the temperature is adjusted to 4° C. The samples are centrifuged at 10,000 rpm at 4° C. to separate the molasses samples into a cake and a liquid whey. The whey and the cake are analyzed for concentration of individual isoflavone compounds.

Table 2 illustrates the change in the proportions between the various forms of isoflavones resulting from the conversion of isoflavone conjugates to isoflavone glucosides as compared to the soy molasses starting material. Isoflavone concentrations are indicated as parts per million(ppm) within the sample, and as percentages of the total amount of the particular isoflavone (the total of the conjugate, glucoside, and aglucone forms) within the liquid or cake portion.

TABLE 2

| Sample | Genistin | 6"-OMAL-Genistin | 6"-OAC-Genistin | Genistein | Daidzin | 6"-OMAL-Daidzin | 6"-OAC-Daidzin | Daidzein | Glycitin | 6"-OMAL Glycitin | Glycitein |
|---|---|---|---|---|---|---|---|---|---|---|---|
| Soy Molasses | | | | | | | | | | | |
| ppm | 4678 | 1329 | 0 | 88 | 3533 | 928 | 210 | 84 | 500 | 105 | 360 |
| % isoflavone | 77 | 22 | 0 | 1 | 74 | 20 | 4 | 2 | 52 | 11 | 37 |
| 1:4 Dilution Whey | | | | | | | | | | | |
| ppm | 2221 | 17 | 0 | 30 | 2652 | 179 | 29 | 21 | 341 | 28 | 0 |
| % isoflavone | 98 | 1 | 0 | 1 | 92 | 6 | 1 | 1 | 92 | 8 | 0 |
| 1:4 Dilution Cake | | | | | | | | | | | |
| ppm | 28621 | 68 | 0 | 261 | 16133 | 192 | 0 | 232 | 1442 | 0 | 66 |
| % isoflavone | 99 | 0 | 0 | 1 | 97 | 1 | 0 | 1 | 96 | 0 | 4 |
| 1:8 Dilution Whey | | | | | | | | | | | |
| ppm | 2852 | 24 | 0 | 36 | 3356 | 187 | 0 | 27 | 406 | 28 | 0 |
| % isoflavone | 98 | 1 | 0 | 1 | 94 | 5 | 0 | 1 | 94 | 6 | 0 |
| 1:8 Dilution Cake | | | | | | | | | | | |
| ppm | 27517 | 101 | 0 | 272 | 12617 | 138 | 0 | 245 | 1146 | 0 | 0 |
| % isoflavone | 99 | 0 | 0 | 1 | 97 | 1 | 0 | 2 | 100 | 0 | 0 |

In all samples subjected to conditions for conversion of isoflavone conjugates to isoflavone glucosides the percentage of isoflavone glucosides in both cake and liquid portions is significantly higher than in the corresponding unconverted soy molasses sample, and the percentage of corresponding isoflavone conjugates in the samples is significantly lower, demonstrating that a large portion of isoflavone conjugates are converted to their glucoside form. Furthermore, upon separation a large proportion of the glucoside isoflavones are separated in the cake to form an isoflavone glucoside enriched material, as can be seen from the relative concentrations of the soy molasses starting material and the whey and cake portions of each sample.

EXAMPLE 3

In another experiment, the conversion of isoflavones to aglucone isoflavones in soy molasses is examined. Isoflavone conjugates in the soy molasses are converted to isoflavone glucosides, and the isoflavone glucosides are then converted to aglucone isoflavones. The extent of conversion of the isoflavone glucosides to aglucone isoflavones is determined by the quantitative decrease of the concentration of the glucoside of an isoflavone family coupled with a corresponding quantitative increase of the percentage of the aglucone of the same isoflavone family.

Soy molasses starting material is diluted 1:4 with water and is analyzed for concentration of individual isoflavone compounds. The pH of the molasses is then adjusted to 11. The soy molasses is held at room temperature for 1 hour to produce a glucoside enriched soy molasses material. The glucoside enriched soy molasses material is analyzed for concentration of individual isoflavone compounds. Four samples are prepared from the glucoside enriched soy molasses material after the pH of the material is adjusted to 4.5. Each sample is inoculated with an enzyme, where the following enzymes are added to the samples, respectively, at 10% by weight of the molasses solids in each sample: G-Zyme 990, Biopectinase 100L, Lactase 50,000, and Alpha-Gal 600L. The samples are then treated at 50° C. for 6 hours to form an aglucone isoflavone enriched soy molasses material. The aglucone isoflavone enriched soy molasses is then analyzed for isoflavone content.

Table 3 illustrates the distribution between the various forms of isoflavones resulting from the previously described testing. Isoflavone concentrations are indicated as parts per million(ppm) within the sample, and as percentages of the total amount of the particular isoflavone (the total of the conjugate, glucoside, and aglucone forms).

TABLE 3

| Sample | Genistin | 6"-OMAL-Genistin | 6"-OAC-Genistin | Genistein | Daidzin | 6"-OMAL-Daidzin | 6"-OAC-Daidzin | Daidzein | Glycitin | 6"-OMAL-Glycitin | Glycitein |
|---|---|---|---|---|---|---|---|---|---|---|---|
| Soy Molasses | | | | | | | | | | | |
| ppm | 4678 | 1329 | 0 | 88 | 3533 | 928 | 210 | 84 | 500 | 105 | 360 |
| % isoflavone | 77 | 22 | 0 | 1 | 74 | 20 | 4 | 2 | 52 | 11 | 37 |
| Glucoside rich soy molasses | | | | | | | | | | | |
| ppm | 6763 | 0 | 0 | 104 | 4377 | 0 | 0 | 43 | 433 | 0 | 0 |
| % isoflavone | 98 | 0 | 0 | 2 | 99 | 0 | 0 | 1 | 100 | 0 | 0 |
| G-Zyme 990, 10% | | | | | | | | | | | |
| ppm | 3903 | 0 | 0 | 1993 | 840 | 0 | 82 | 2331 | 346 | 0 | 114 |

TABLE 3-continued

| Sample | Genistin | 6"-OMAL-Genistin | 6"-OAC-Genistin | Genistein | Daidzin | 6"-OMAL-Daidzin | 6"-OAC-Daidzin | Daidzein | Glycitin | 6"-OMAL-Glycitin | Glycitein |
|---|---|---|---|---|---|---|---|---|---|---|---|
| % isoflavone Biopectinase 100 L 10% | 66 | 0 | 0 | 44 | 27 | 0 | 2 | 71 | 75 | 0 | 25 |
| ppm | 2865 | 0 | 0 | 2919 | 541 | 0 | 94 | 2701 | 195 | 0 | 237 |
| % isoflavone Lactase 50,000, 10% | 50 | 0 | 0 | 50 | 16 | | 3 | 81 | 45 | 0 | 55 |
| ppm | 0 | 0 | 0 | 4601 | 0 | 0 | 92 | 2875 | 0 | 0 | 366 |
| % isoflavone Alpha-Gal 600 L. 10% | 0 | 0 | 0 | 100 | 0 | 0 | 3 | 97 | 0 | 0 | 100 |
| ppm | 28 | 0 | 0 | 4566 | 0 | 0 | 89 | 2882 | 0 | 0 | 356 |
| % isoflavone | 1 | 0 | 0 | 99 | 0 | 0 | 3 | 97 | 0 | 0 | 100 |

The aglucone isoflavone content of the enzymatically treated samples is significantly higher than the soy molasses and the glucoside enriched soy molasses material, indicating that the enzymatic treatment converted substantial amounts of glucoside isoflavones to aglucone isoflavones. Selection of the proper enzyme, enzyme concentration, pH and temperature for the conversion permits conversion of substantially all of the isoflavone glucosides to aglucone isoflavones, as demonstrated by the isoflavone distribution in the Lactase 50,000 and Alpha-Gal 600L samples.

EXAMPLE 4

In a final experiment, the isoflavone content of an isoflavone enriched material, an isoflavone glucoside enriched material, and an aglucone isoflavone enriched material is examined and the distribution of the isoflavones in the materials is compared. Soy molasses is diluted to a 1:4 ratio with water. A sample of the diluted soy molasses is adjusted to a pH of 4.5, is chilled to a temperature of 0.6° C. in an ice bath for 30 minutes, and is centrifuged at a rate of 3000 rpm for 30 minutes to separate a cake of isoflavone enriched material. The remaining diluted soy molasses is then adjusted to a pH of 11 with sodium hydroxide and is treated at 50° C. for 1 hour to convert isoflavone conjugates in the molasses to isoflavone glucosides. A sample of the glucoside enriched molasses is adjusted to a pH of 4.5, is chilled to a temperature of 0.6° C. in an icebath for 30 minutes, and is centrifuged at a rate of 3000 rpm for 30 minutes to separate a cake of isoflavone glucoside enriched material. The remaining isoflavone glucoside enriched soy molasses material is adjusted to pH 4.5, and the enzyme G-Zyme 990 is added to the material at a concentration of 2.6g enzyme/100g of molasses material. The enzyme and the isoflavone glucoside enriched soy molasses material are then treated at 50° C. for 18 to 20 hours to convert the isoflavone glucosides to aglucone isoflavones. A sample of the aglucone isoflavone enriched soy molasses material is chilled to a temperature of 0.6° C. in an icebath for 30 minutes, and is centrifuged at a rate of 3000 rpm for 30 minutes to separate a cake of aglucone isoflavone enriched material. The recovered cakes of isoflavone enriched material, isoflavone glucoside enriched material, and aglucone isoflavone enriched material are then analyzed for isoflavone content.

Table 4 below shows the distribution of the isoflavones in the cakes of isoflavone enriched material, isoflavone glucoside enriched material, and aglucone isoflavone enriched material. Isoflavone distribution is indicated as percentages of the total amount of the particular isoflavone (the total of the conjugate, glucoside, and aglucone forms).

TABLE 4

| Sample | Genistin | 6"-OMAL-Genistin | 6"-OAC-Genistin | Genistein | Daidzin | 6"-OMAL-Daidzin | 6"-OAC-Daidzin | Daidzein | Glycitin | 6"-OMAL-Glycitin | Glycitein |
|---|---|---|---|---|---|---|---|---|---|---|---|
| Isoflavone rich material | | | | | | | | | | | |
| % isoflavone | 83 | 16 | 0 | 1 | 81 | 12 | 5 | 1 | 40 | 8 | 52 |
| Glucoside rich material | | | | | | | | | | | |
| % isoflavone | 99 | 0 | 0 | 1 | 99 | 0 | 0 | 1 | 95 | 0 | 5 |
| Aglucone rich material | | | | | | | | | | | |
| % isoflavone | 3 | 0 | 0 | 97 | 0 | 0 | 0 | 100 | 54 | 18 | 28 |

The effectiveness of the conversion steps can be seen in the isoflavone distribution of the materials. The isoflavone glucoside enriched material contains significantly higher amounts of isoflavone glucosides than the isoflavone enriched material and the aglucone isoflavone material, having an isoflavone content which is comprised of almost entirely isoflavone glucosides. The aglucone isoflavone enriched material contains significantly higher amounts of aglucone isoflavones than the isoflavone glucoside enriched material and the isoflavone enriched material, having an isoflavone content which is comprised of almost entirely aglucone isoflavones.

In the above examples, all percentages indicated for 6"-OMal-genistin, 6"-OAc-genistin, 6"-OMal-daidzin, 6"-OAc-daidzin, glycitin, 6"-OMal-glycitin, and glycitein are calculated values. The following is a description of a method for quantifying isoflavones in soy products. The isoflavones are extracted from soy products by mixing 0.75 gram of sample (spray dried or finely ground powder) with 50 ml of 80/20 methanol/water solvent. The mixture is shaken for 2 hours at room temperature with an orbital shaker. After 2 hours, the remaining undissolved materials are removed by filtration through Whatman No. 42 filter paper. Five ml of the filtrate are diluted with 4 ml of water and 1 ml of methanol.

The extracted isoflavones are separated by HPLC (High Performance Liquid Chromatography)using a Hewlett Packard C18 Hypersil reverse phase column. The isoflavones are injected onto the column and eluted with a solvent gradient starting with 88% methanol, 10% water, and 2% glacial acetic acid and ending with 98% methanol and 2% glacial acetic acid. At a flow rate of 0.4 ml/min, all the isoflavones-genistin, 6"-0-acetylgenistin, 6"-0-malonylgenistin, genistein, daidzin, 6"-0-acetyldaidzin, 6"-0-malonyldaidzin, daidzin, glycitin and its derivatives and glycitein—are clearly resolved. Peak detection is by UV absorbence at 260 mm. Identification of the peaks was performed by HPLC-mass spectrometer.

Quantification is achieved by using pure standards (genistin, genistein, daidzin and daidzein) obtained from Indofine Chemical Company, Sommerville, N.J. Response factors (integrated area/concentration) are calculated for each of the above compounds and are used to quantitate unknown samples. For the conjugated forms for which no pure standards are available, response factors are assumed to be that of the parent molecule but corrected for molecular weight difference. The response factor for glycitin is assumed to be that for genistin corrected for molecular weight difference. This method provides the quantities of each individual isoflavone. For convenience, total genistein, total daidzein and total glycitein can be calculated, and represent the aggregate weight of these compounds if all the conjugated forms are converted to their respective unconjugated forms. These totals can also be measured directly by a method using acid hydrolysis to convert the conjugated forms.

The foregoing are merely preferred embodiments of the invention. Various changes and alterations can be made without departing from the spirit and broader aspects thereof as set forth in the appended claims, which are to be interpreted in accordance with the principals of patent law including the Doctrine of Equivalents.

What is claimed is:

1. An isoflavone material comprising a solid material separated from a soy molasses material wherein said solid material contains at least two isoflavones, where at least one of said isoflavones in said solid material is glycitein and at least one of said isoflavones in said solid material is an isoflavone glucoside.

2. The isoflavone material of claim 1 wherein said isoflavone glucoside is genistin.

3. The isoflavone material of claim 1 wherein said isoflavone glucoside is daidzin.

4. The isoflavone material of claim 1 wherein said isoflavone glucoside is glycitin.

5. The isoflavone material of claim 1 wherein said isoflavone material contains at least three isoflavones.

6. An isoflavone material comprising a solid material separated from a soy molasses material wherein said solid material contains at least two isoflavones, where at least one of said isoflavones in said solid material is glycitein and at least one of said isoflavones in said solid material is an isoflavone glucoside conjugate.

7. The isoflavone material of claim 6 wherein said isoflavone material contains at least three isoflavones.

8. An isoflavone material comprising a solid material separated from a soy molasses material wherein said solid material contains at least two isoflavones, where at least one of said isoflavones is glycitin and at least one of said isoflavones in said solid material is an aglucone isoflavone.

9. The isoflavone material of claim 8 wherein said aglucone isoflavone is genistein.

10. The isoflavone material of claim 8 wherein said aglucone isoflavone is daidzein.

11. The isoflavone material of claim 8 wherein said isoflavone material contains at least three isoflavones.

* * * * *